United States Patent [19]

Dumoulin et al.

[11] Patent Number: 5,730,134
[45] Date of Patent: Mar. 24, 1998

[54] SYSTEM TO MONITOR TEMPERATURE NEAR AN INVASIVE DEVICE DURING MAGNETIC RESONANCE PROCEDURES

[75] Inventors: Charles Lucian Dumoulin, Ballston Lake; Ronald Dean Watkins, Niskayuna; Robert David Darrow, Scotia; Steven Peter Souza, Williamstown, all of N.Y.

[73] Assignee: General Electric Company, Schenectady, N.Y.

[21] Appl. No.: 714,840

[22] Filed: Sep. 9, 1996

[51] Int. Cl.$^6$ ............................................. A61B 5/00
[52] U.S. Cl. ................... 128/653.1; 128/653.2; 128/736
[58] Field of Search ............... 128/653.1, 653.2, 128/653.5, 736, 630, 664, 665; 356/128; 374/130, 132; 607/96, 100, 101, 102; 324/309, 315

[56] References Cited

U.S. PATENT DOCUMENTS

| | | | |
|---|---|---|---|
| 4,558,279 | 12/1985 | Ackerman et al. | 324/315 |
| 5,015,102 | 5/1991 | Yamaguchi | 374/107 |
| 5,207,222 | 5/1993 | Koizumi et al. | 128/653.2 |
| 5,284,144 | 2/1994 | Delannoy et al. | 128/653.2 |
| 5,304,214 | 4/1994 | Deford et al. | 607/105 |
| 5,307,808 | 5/1994 | Dumoulin et al. | |
| 5,307,812 | 5/1994 | Hardy et al. | 128/653.2 |
| 5,318,025 | 6/1994 | Dumoulin et al. | |
| 5,323,778 | 6/1994 | Kandarpa et al. | 128/653.2 |
| 5,353,795 | 10/1994 | Souza . | |
| 5,485,839 | 1/1996 | Aida et al. | 128/653.1 |
| 5,553,618 | 9/1996 | Suzuki et al. | 128/653.1 |
| 5,599,346 | 2/1997 | Edwards et al. | 606/41 |

OTHER PUBLICATIONS

"Fluoroptic Thermometer Model 790 Operator's Guide", pp. 4.1–4.6. Luxtron Corp., 2775 Northwestern Parkway, Santa Clara, CA 95051–0903, Copyright Dec. 1992.

Primary Examiner—Marvin M. Lateef
Assistant Examiner—Eleni Mantis Mercader
Attorney, Agent, or Firm—Lawrence P. Zale; Marvin Snyder

[57] ABSTRACT

A temperature monitoring system employs a temperature detection means incorporated into an invasive device intended to be placed within a body during a magnetic resonance procedure. The temperature monitoring system is used to monitor temperature rises in tissue arising from the creation of electric fields within the tissue. These electric fields are created by the application of RF pulses during the course of a magnetic resonance procedure which induce electrical current in the invasive device. It the detected temperature rise exceeds a selected threshold, the temperature monitoring system can cause the magnetic resonance imaging system to either reduce RF power or terminate the procedure. An optical coupling may be used between the imaging or tracking RF coil and the MR receiver to eliminate heating induced by the application of RF pulses during the procedure.

6 Claims, 3 Drawing Sheets

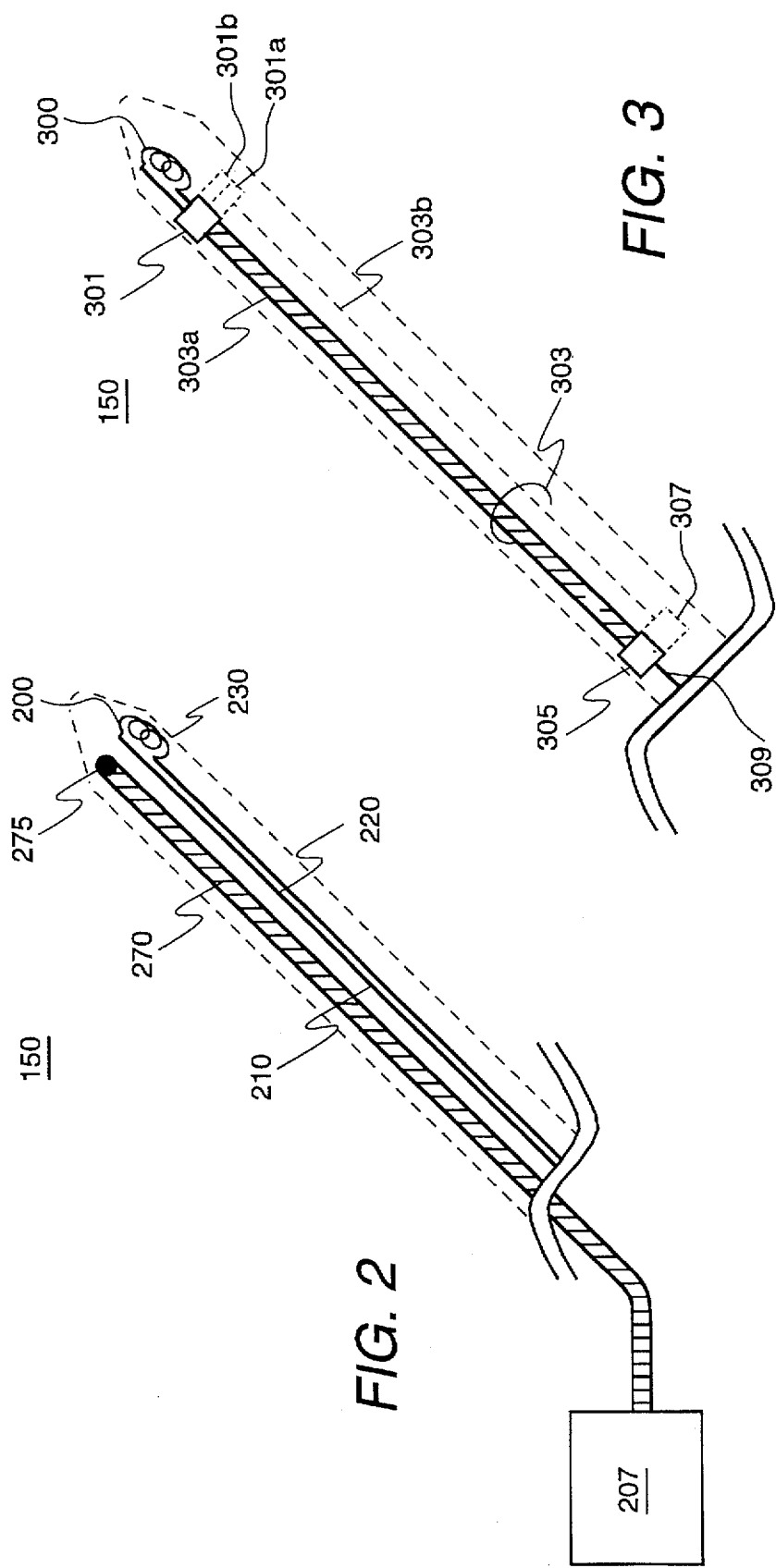

5,730,134

SYSTEM TO MONITOR TEMPERATURE NEAR AN INVASIVE DEVICE DURING MAGNETIC RESONANCE PROCEDURES

FIELD OF THE INVENTION

The present invention relates to medical procedures in which a device is inserted into a body, and more particularly concerns medical procedures in which such a device is used while the body is in a magnetic resonance scanner.

DESCRIPTION OF RELATED ART

Several methods of following an interventional device within the body of a patient using magnetic resonance (MR) are described in U.S. Pat. No. 5,307,808; "Tracking System And Pulse Sequences To Monitor The Position Of A Device Using Magnetic Resonance", U.S. Pat. No. 5,318,205; "Tracking System To Monitor The Position And Orientation Of A Device Using Multiplexed Magnetic Resonance Detection"; and U.S. Pat. No. 5,353,795 "Tracking System To Monitor The Position Of A Device Using Multiplexed Magnetic Resonance Detection", by Charles L. Dumoulin, Steven P. Souza and Robert Darrow and assigned to the present assignee, and hereby incorporated by reference. These methods employ Magnetic Resonance Signal generation and detection to locate and follow an interventional device and do not have the undesirable attributes associated with X-ray monitoring.

One aspect of magnetic resonance tracking methods is that the interventional device incorporates a cable or wire to bring magnetic resonance signals detected within the body out to the imaging and tracking system. An MR imaging or tracking coil is placed within or on the surface of a subject and is typically connected to an external receiver by a coaxial cable. One consequence of placing conducting material within the body during a magnetic resonance procedure is that the radiofrequency (RF) pulses used for image formation and device tracking can induce currents in the conductor. These currents can result in the creation of strong electric fields at the ends of the conductor. If the end of the conductor is surrounded by conducting tissue such as blood, these strong electric fields will induce currents in the tissue and cause heating. The amount of heating within the tissue is related to the power and duty cycle of the RF pulse. Stronger and more frequently applied RF pulses create greater amounts of heating. The amount of heating is also indirectly related to the strength of the static magnetic field used in magnetic resonance procedures since greater RF power is required to nutate the nuclear spins in higher magnetic fields.

If the amount of heat deposited within conducting tissue near an interventional device causes a temperature rise of less than about four degrees Celsius, then no damage to the tissue will occur. If the heat deposited causes the temperature to rise in excess of about four degrees Celsius, however, reversible or irreversible tissue damage can occur.

It should be noted that placement of wires or other conducting structures within the body during a magnetic resonance examination may be desirable for reasons other than tracking of a device. For example, small magnetic resonance receive coils can be used to make images of localized anatomy such as the wall of a blood vessel. Alternatively, it may be desirable to place other medical devices such as endoscopes or catheter guide-wires which could result in localized tissue heating during magnetic resonance exams.

Currently, there is a need for a method of monitoring and reducing the heating due to a device placed within the body during a magnetic resonance imaging exam.

SUMMARY OF THE INVENTION

Devices intended to be placed within a body during a magnetic resonance (MR) procedure are augmented with one or more thermal sensors. Each sensor is placed within the device to monitor temperature increases in a selected region within or near the device.

Several temperature monitoring methods are possible. For example, thermocouples can be used to monitor temperature increases, although care should be taken since the presence of the thermocouple leads could contribute to the undesired heating. More desirable methods involve the use of light to measure temperature since non-conducting optical fibers can be employed. One optical means of monitoring temperature employs a fluorescent substance having a fluorescence decay time which is a function of temperature. A temperature monitoring means using this physical principle can be readily constructed by placing a portion of the phosphor on the end of a optical fiber while both exciting and monitoring the phosphor decay at the other end.

Once the device has been modified to permit the monitoring of temperature, the instantaneous value of the temperature can be used in several different ways. For example, the temperature can be displayed to the attending clinician. Alternatively, the temperature can also be propagated to a safety interlock means of the scanner which will cause the magnetic resonance scanner to reduce its RF power and/or duty cycle or terminate the procedure when temperature increases above a selected threshold are detected. Upon reduction of RF power it may be desirable to generate a visual or audio alarm for the operator of the magnetic resonance system.

Additionally, wiring connecting an MR imaging or tracking coil with a receiver can be replaced with an optical fiber and a transducer at each end for converting between electrical and optical signals.

OBJECTS OF THE INVENTION

It is an object of the present invention to provide a system for the monitoring of heating within a body due to the presence of an invasive device during a magnetic resonance scan.

It is another object of the present invention to provide a method of reducing or terminating the RF power generated by a magnetic resonance scanner whenever heating of tissue above a selected threshold is detected within a body during an MR examination.

It is another object of the present invention to provide a method of reducing the RF duty cycle generated by a magnetic resonance scanner whenever heating of tissue above a selected threshold is detected within a body during an MR examination.

It is another object of the present invention to reduce RF heating in the vicinity of a subject being imaged.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawings in which:

FIG. 2 is an illustration showing an RF coil and a fiber-optic temperature sensor incorporated into a medical device intended to be inserted into the body of a subject.

FIG. 3 is an illustration of an optical coupling replacing wiring between an MR imaging or tracking coil and MR receiver electronics.

DETAILED DESCRIPTION OF THE INVENTION

Figure 1:
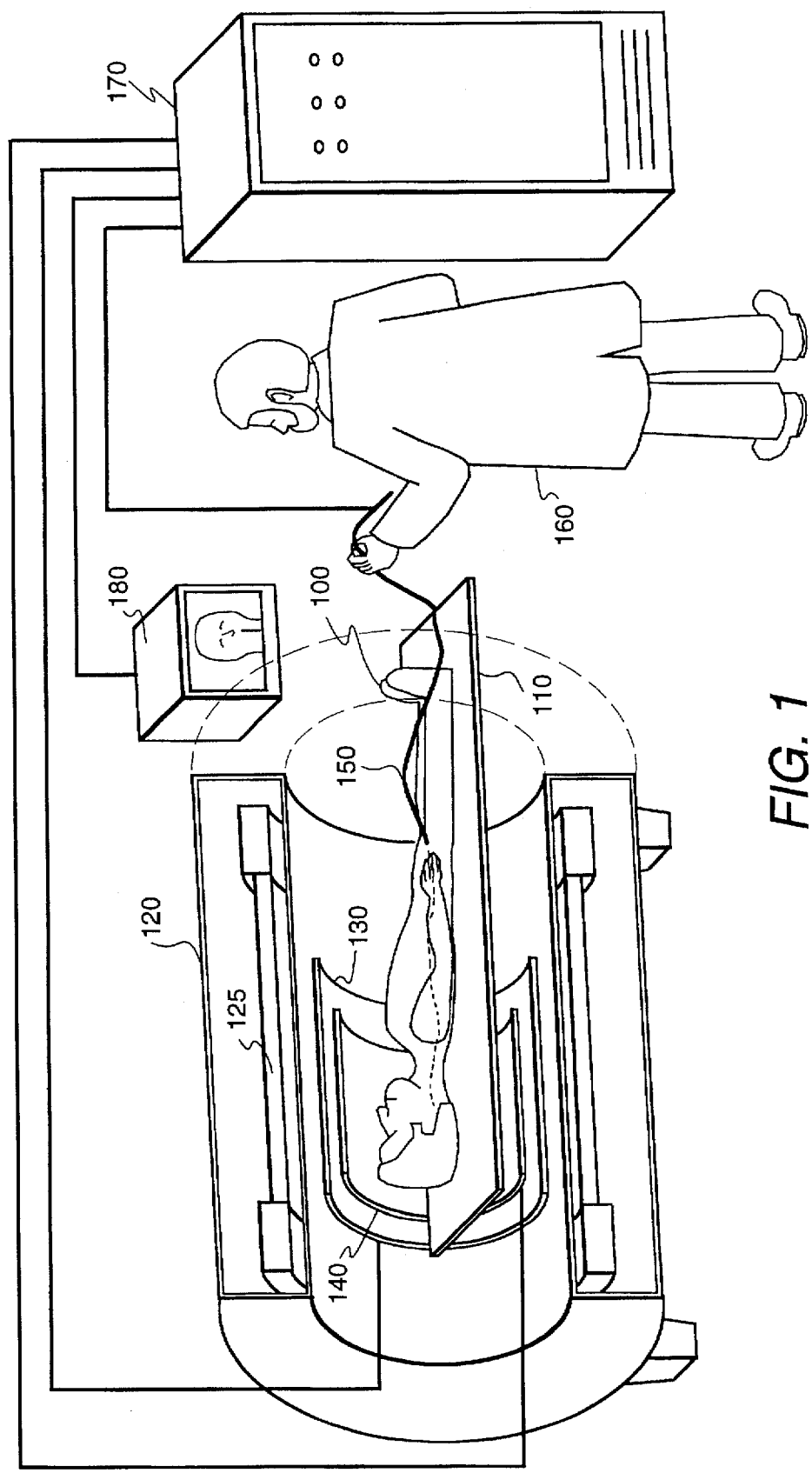
FIG. 1 is a perspective view of one embodiment of the present invention in operation tracking the location of a device in a subject.

In FIG. 1, a subject 100 on a support table 110 is placed in a homogeneous magnetic field generated by a magnet 125 in magnet housing 120. Magnet 125 and magnet housing 120 have cylindrical symmetry and are shown sectioned in half to reveal the position of subject 100. A region of subject 100 into which a device 150, shown as a catheter, is inserted, is located in the approximate center of the bore of magnet 125. Subject 100 is surrounded by a set of cylindrical magnetic field gradient coils 130 which create magnetic field gradients of predetermined strength at predetermined times. Gradient coils 130 generate magnetic field gradients in three mutually orthogonal directions.

An external coil 140 also surrounds the region of interest of subject 100. Coil 140 is shown as a cylindrical external coil which has a diameter sufficient to encompass the entire subject. Other geometries, such as smaller cylinders specifically designed for imaging the head or an extremity can be used instead. Non-cylindrical external coils, such as surface coils, may alternatively be used.

External coil 140 radiates radio frequency (RF) energy into subject 100 at predetermined times and with sufficient power at the predetermined frequency that nutates nuclear magnetic spins of subject 100 in a fashion well known to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

Device 150 is inserted into subject 100 by an operator 160, and may be a guide wire, a catheter, an endoscope, a laparoscope, a biopsy needle or similar device. If it is desirable to follow device 150 in real-time using magnetic resonance, device 150 can be made to contain an RF coil which detects MR signals generated in the subject responsive to the radio frequency field created by external coil 140. Since the RF coil is small, the region of sensitivity is also small. Consequently, the detected signals have Larmor frequencies which arise only from the strength of the magnetic field in the immediate vicinity of the coil. These detected signals are sent to an imaging and tracking unit 170 where they are analyzed. The position of device 150 is determined in imaging and tracking unit 170 and is displayed on a display means 180. In the preferred embodiment of the invention the position of device 150 is displayed on display means 180 by superposition of a graphic symbol on a conventional MR image driven by a superposition means (not shown), such as a video graphics subsystem capable of superimposing an icon over an image.

In alternative embodiments of the invention, the graphic symbol representing device 150 is superimposed on diagnostic images obtained with other imaging systems such as a computed tomography (CT) scanner, a Positron Emission Tomography system or ultrasound scanner. Other embodiments of the invention display the position of the device numerically or as a graphic symbol without reference to a diagnostic image.

An embodiment of device 150 is shown in greater detail in FIG. 2. A small RF coil 200 is electrically coupled to the MR system via conductors 210 and 220. In the preferred embodiment of this invention, conductors 210 and 220 form a co-axial pair. Conductors 210 and 220 and RF coil 200 are encased in an outer shell 230 of device 2150. The MR signal arising from the tissue surrounding device 150 is detected. Device 150 also incorporates an optical fiber 270 placed so that the distal end of the fiber is near small RF coil 200. In the current embodiment of the present invention the proximal end is attached to a light source/detector 207 and the distal end of fiber 270 incorporates a small amount of a selected fluorescent substance 275. Fluorescent substance 275 absorbs light propagated to the distal end of fiber 270 and re-emits the light. The re-emission of light occurs over a period of time after the initial light is absorbed with a decay constant which can be measured and used to compute the temperature of fluorescent substance 275. This is described in the "Fluoroptic Thermometer Model 790 Operator's Guide", pp. 4.1–4.6, Luxtron Corp, 2775 Northwestern Parkway, Santa Clara, Calif. 95051-0903, copyright Dec. 1992.

Wiring within the subject may be replaced with optical fiber, as shown in FIG. 3, for the purpose of preventing RF induced heating. An RF coil 300 is located within the subject. A first transducer circuit 301 is connected to RF coil 300. First transducer circuit 301 is coupled to an optical fiber 303, and converts electronic signals to modulated light typically at visible or near-infrared wavelengths. First transducer circuit 301 may be unidirectional passing signal to RF coil 300, unidirectional passing signals from RF coil 300 to optical fiber 303, or bi-directional. This includes situations in which RF coil 300 is transmitting, receiving, or both, respectively.

RF coil 300 may receive MR signals for MR tracking or for localized MR imaging.

At the other end of optical fiber 303, a second transducer circuit 305, operates in a manner opposite that of first transducer circuit 301. For example, if RF coil 300 is receiving an MR response signal, its electrical signal is converted to a modulated optical signal by first transducer circuit 301 passed through optical fiber 303, converted back to its original electrical signal by second transducer circuit 305, then passed onto the MR receiver to provide an MR image of the subject and/or RF coil location. First transducer circuit 301 may be powered by a small energy storage device 301b (battery or capacitor) and a photo-diode 301a. Light may be passed from a light source 307 through optical fiber 303 to first transducer circuit 301 and photodiode 301a, creating current which charges the energy storage device 301b, thereby providing power to first transducer circuit 301.

Alternatively, first transducer circuit 301 could have separate optical pathways 303a, 303b or fibers, in which the signal passes through one pathway 303a while power passes to transducer circuit 303b in another separate pathway.

Figure 4:
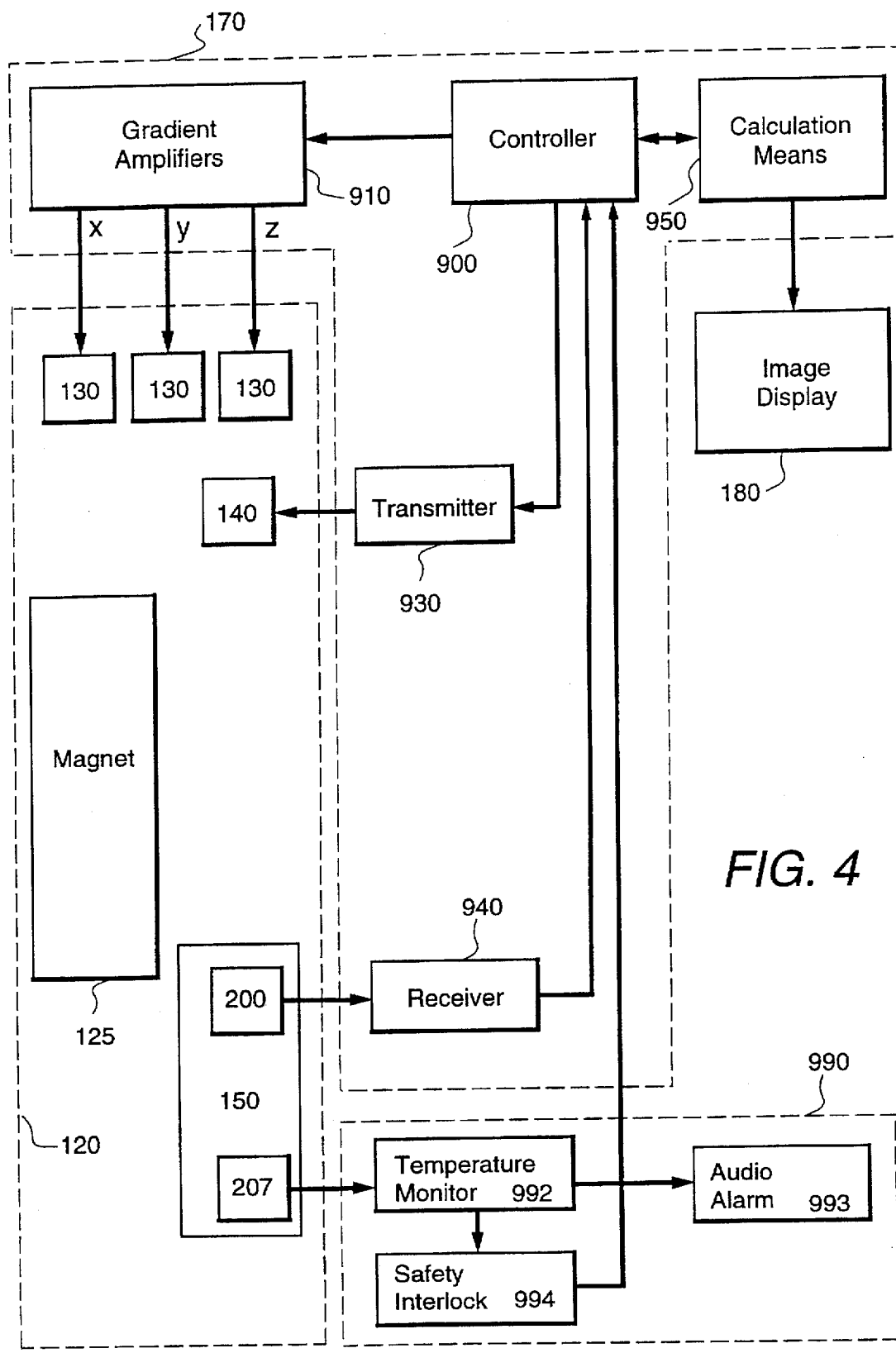
FIG. 4 is a system block diagram illustrating one embodiment of a thermal safety subsystem suitable for incorporation into a magnetic resonance scanner.

FIG. 4 is a block diagram of an MR system suitable for imaging and device tracking. The system comprises a controller 900 which provides control signals to a set of magnetic field gradient amplifiers 910. These amplifiers drive magnetic field gradient coils 130 situated within magnet housing 120 (FIG. 1). Gradient coils 130 are capable of generating magnetic field gradients in three mutually orthogonal directions. Controller 900 also generates signals which are sent to a transmitter means 930. These signals from controller 900 cause transmitter means 930 to generate RF pulses at a selected frequency and of suitable power to nutate selected spins in the region of the subject situated within external coil 140 which, in turn, is situated within the bore of magnet 125. An MR signal is induced in RF coil 200, (FIG. 2) connected to a receiver means 940 which may be connected through optical coupling of FIG. 3. Receiver means 940 processes the MR signal by amplifying, demodulating, filtering and digitizing it. Controller 900 also collects signals from receiver means 940 and propagates it to a calculation means 950 where it is processed. Calculation means 950 applies a Fourier transformation to the signal received from controller 900 to arrive at a position of coil 200. The results calculated by calculation means 950 are displayed on an image display means 180.

The MR system of FIG. 4 also incorporates a safety monitoring subsystem 990 which includes a temperature monitoring means 992 and a safety interlock means 994.

In the preferred embodiment of the present invention a light source/detector 207 of FIG. 2 generates light pulses which are propagated to fluorescent substance 275 located at the distal end of optical fiber 270 located in device 150. Temperature monitoring means 992 of FIG. 4 is coupled to source detector 207 which detects the fluorescent decay. Temperature monitoring means 992 then measures the decay rate and computes the temperature of fluorescent substance 275. It should be noted that the spirit of the present invention is not limited to temperature detection based upon fluorescent decay, but includes all temperature monitoring means, such as a thermistor or thermocouple.

In the present embodiment, safety interlock means 994 is connected to controller 900. If temperature monitoring means 992 detects a rise in temperature in excess of a selected threshold, then a signal is propagated from safety interlock means 994 to controller means 900 causing controller means to either reduce RF power, reduce the RF duty cycle or terminate the current magnetic resonance RF and gradient pulse sequence.

Temperature monitoring means 992 can also be used to trigger an audio alarm 993 when a threshold has been exceeded to notify the operator of the rise in temperature.

While several presently preferred embodiments of the novel temperature monitoring subsystem for magnetic resonance procedures have been described in detail herein, many modifications and variations will now become apparent to those skilled in the art. It is, therefore, to be understood that the appended claims are intended to cover all such modifications and variations as fall within the true spirit of the invention.

What is claimed is:

1. A safety subsystem for use within a magnetic resonance (MR) imaging system having a radiofrequency (RF) transmitter device which transmits RF power into a subject, for monitoring temperature of an invasive device and adjacent tissue of said subject during imaging and reducing said RF power applied to said subject; comprising:

a) means for detecting temperature within a selected portion of said invasive device used during a magnetic resonance imaging procedure;

b) temperature monitoring means for determining if the detected temperature exceeds a selected threshold; and c) means for reducing radiofrequency (RF) power of said RF transmitter device of said MR imaging system responsive to the temperature detected within the invasive device.

2. The safety subsystem recited in claim 1, wherein the temperature monitoring means employs light to measure temperature.

3. The safety subsystem recited in claim 2, wherein the temperature monitoring means measures the decay time of an optical fluorescence to measure temperature.

4. The safety subsystem recited in claim 1, wherein the temperature monitoring means uses a thermocouple to measure temperature.

5. The safety subsystem recited in claim 1, further comprising a display device to indicate the temperature detected within the invasive device to an operator of said MR imaging device.

6. The safety subsystem of claim 1 further comprising a sound device coupled to the temperature monitoring means to indicate when a threshold has been exceeded.

\* \* \* \* \*